US006225122B1

(12) United States Patent
Sah et al.

(10) Patent No.: US 6,225,122 B1
(45) Date of Patent: May 1, 2001

(54) HUMAN SPINAL CORD CELL LINES AND METHODS OF USE THEREFOR

(75) Inventors: Dinah W. Y. Sah; Ronghao Li, both of San Diego, CA (US)

(73) Assignee: Signal Pharmaceuticals, Inc., San Diego, CA (US)

(*) Notice: Subject to any disclaimer, the term of this patent is extended or adjusted under 35 U.S.C. 154(b) by 0 days.

(21) Appl. No.: 09/059,790

(22) Filed: Apr. 13, 1998

Related U.S. Application Data

(60) Provisional application No. 60/076,567, filed on Mar. 2, 1998.

(51) Int. Cl.$^7$ ............................ C12N 15/85; C12N 15/22; C12N 15/12; C12N 15/33
(52) U.S. Cl. ........................ 435/467; 435/368; 435/377; 536/23.5; 536/23.72
(58) Field of Search ..................................... 435/455, 467, 435/368, 377; 536/23.5, 23.72

(56) References Cited

FOREIGN PATENT DOCUMENTS

| 2 294 946 | 5/1996 | (GB) . |
| WO 97/30168 | 8/1997 | (WO) . |
| WO 98/10058 | 3/1998 | (WO) . |

OTHER PUBLICATIONS

Kato et al. Overlapping and additive effects on neurotrophins and CNTF on cultured human spinal cord neurons. Experimental Neurobiology vol. 130 pp. 196–201, 1994.*

Tornatore et al. Expression of tyrosine hydroxylase in an immortalized human fetal astrocyte cell line; in vitro characterization and engraftment into the rodent striatum. Cell Transplantation vol. 5 pp. 145–163, 1996.*

Johe et al. Sincle factors direct the differentiation of stem cells from the fetal and adult central nervous system. Genes and Development vol. 10 pp. 3129–3140, 1996.*

Li et al., "Conditionally Immortalized Neuronal Restricted Cell Lines From Human Spinal Cord," *Society For Neuroscience Abstracts* 24 (1–2): p. 1529, 1998.

Cashman et al., "Neuroblastoma × Spinal Cord (NSC) Hybrid Cell Lines Resemble Developing Motor Neurons," *Developmental Dynamics* 194: 209–221, 1992.

Deloulme et al., "Establishment of Pure Neuronal Cultures From Fetal Rat Spinal Cord and Proliferation of the Neuronal Precursor Cells in the Presence of Fibroblast Growth Factor," *Journal of Neuroscience Research* 29: 499–509, 1991.

Hoshimaru et al., "Differentiation of the immortalized adult neuronal progenitor cell line HC2S2 into neurons by regulatable suppression of the v–myc oncogene," *Proc. Natl. Acad. Sci. USA* 93: 1518–1523, 1996.

Kalyani et al., "Neuroepithelial Stem Cells from the Embryonic Spinal Cord: Isolation, Characterization, and Clonal Analysis," *Developmental Biology* 186: 202–223, 1997.

Kim et al., "Human and Rodent Spinal Cord Neurons in Culture," in *Advances in Neurology vol. 56:* Amyotropic Lateral Sclerosis and Other Motor Neuron Diseases, Lewis P. Rowland (ed.), Raven Press, Ltd., 1991, Chapter 4, pp. 57–66.

Sah et al., "Bipotent progenitor cell lines from the human CNS," *Nature Biotechnology* 15: 574–580, 1997.

Salazar–Grueso et al., "Embryonic mouse spinal cord motor neuron hybrid cells," *NeuroReport* 2: 505–508, 1991.

Whittemore et al., "Isolation and Characterization of Conditionally Immortalized Astrocyte Cell Lines Derived From Adult Human Spinal Cord," *GLIA* 10: 211–226, 1994.

Aloisi et al., "Developmental Appearance, Antigenic Profile, and Proliferation of Glial Cells of the Human Embryonic Spinal Cord: An Immunocytochemical Study Using Dissociated Cultured Cells," *GLIA* 5: 171–181, 1992.

Bannerman et al., "Effects of FGF–1 and FGF–2 on GD3 Immunoreactive Spinal Neuroepithelial Cells," *Journal of Neuroscience Research* 45: 549–557, 1996.

Barlett et al., "Immortalization of mouse neural precursor cells by the c–myc oncogene," *Proc. Natl. Acad. Sci. USA* 85: 3255–3259, 1988.

Engel and Wolswijk, "Oligodendrocyte–Type–2 Astrocyte (O–2A) Progenitor Cells Derived From Adult Rat Spinal Cord: In Vitro Characteristics and Response to PDGF, bFGF and NT–3," *GLIA* 16: 16–26, 1996.

Frederiksen et al., "Immortalization of Precursor Cells from the Mammalian CNS," *Neuron* 1: 439–448, 1988.

Geller and Dubois–Dalcq, "Antigenic and Functional Characterization of a Rat Central Nervous System–derived Cell Line Immortalized by a Retroviral Vector," *The Journal of Cell Biology* 107: 1977–1986, 1988.

Lachyankar et al., "Embryonic Precursor Cells That Express Trk Receptors: Induction of Different Cell Fates by NGF, BDNF, NT–3, and CNTF," *Experimental Neurology* 144: 350–360, 1997.

Leber et al., "Lineage, Arrangement, and Death of Clonally Related Motoneurons in Chick Spinal Cord," *The Journal of Neuroscience* 10(7): 2451–2462, 1990.

Leber and Sanes, "Migratory Paths of Neurons and Glia in the Embryonic Chick Spinal Cord," *The Journal of Neuroscience* 15(2): 1236–1248, 1995.

(List continued on next page.)

*Primary Examiner*—John S. Brusca
(74) *Attorney, Agent, or Firm*—Pennie & Edmonds LLP (57) ABSTRACT

Conditionally-immortalized human spinal cord cell lines are provided. Such cell lines, which may be clonal, may be used to generate neurons, including motoneurons. The cell lines and/or differentiated cells may be used for the development of therapeutic agents to prevent and treat a variety of spinal cord-related diseases and injuries. The cell lines and/or differentiated cells may also be used in assays and for the general study of spinal cord cell development and differentiation.

15 Claims, 10 Drawing Sheets

OTHER PUBLICATIONS

Levison and Goldman, "Multipotential and Lineage Restricted Precursors Coexist in the Mammalian Perinatal Subventricular Zone," *Journal of Neuroscience Research* 48: 83–94, 1997.

Li et al., "Multiple Factors Control the Proliferation and Differentiation of Rat Early Embryonic (Day 9) Neuroepithelial Cells," *Endocrine* 5(2): 205–217, 1996.

Luskin et al., "Neuronal Progenitor Cells Derived from the Anterior Subventricular Zone of the Neonatal Rat Forebrain Continue to Proliferate in Vitro and Express a Neuronal Phenotype," *Molecular and Cellular Neuroscience* 8: 351–366, 1997.

Marti et al., "Requirement of 19K form of Sonic hedgehog for induction of distinct ventral cell types in CNS explants," *Nature* 375: 322–325, 1995.

Matsumoto et al., "Ganglioside characterization of a cell line displaying motor neuron–like phenotype: GM2 as a possible major ganglioside in motor neurons," *Journal of Neurological Sciences* 131: 111–118, 1995.

Mayer–Proschel et al., "Isolation of Lineage–Restricted Neuronal Precursors from Multipotent Neuroepithelial Stem Cells," *Neuron* 19: 773–785, 1997.

Mellon et al., "Immortalization of Hypothalamic GnRH Neurons by Genetically Targeted Tumorigenesis," *Neuron* 5: 1–10, 1990.

Ono et al., "Early Development of the Oligodendrocyte in the Embryonic Chick Metencephalon," *Journal of Neuroscience Research* 48: 212–225, 1997.

Pringle and Richardson, "A singularity of PDGF alpha–receptor expression in the dorsoventral axis of the neural tube may define the origin of the oligodendrocyte lineage," *Development* 117: 525–533, 1993.

Rao and Mayer–Proschel, "Glial–Restricted Precursors Are Derived from Multipotent Neuroepithelial Stem Cells," *Developmental Biology* 188: 48–63, 1997.

Ray and Gage, "Spinal Cord Neuroblasts Proliferate in Response to Basic Fibroblast Growth Factor," *The Journal of Neuroscience* 14(6): 3548–3564, 1994.

Renfranz et al., "Region–Specific Differentiation of the Hippocampal Stem Cell Line HiB5 upon Implantation into the Developing Mammalian Brain," *Cell* 66: 713–729, 1991.

Ryder et al., "Establishment and Characterization of Multipotent Neural Cell Lines Using Retrovirus Vector–Mediated Oncogene Transfer," *Journal of Neurobiology* 21 (2): 356–375, 1990.

Satoh and Kim, "Proliferation and Differentiation of Fetal Human Oligodendrocytes in Culture," *Journal of Neuroscience Research* 39: 260–272, 1994.

Snyder et al., "Multipotent Neural Cell Lines Can Engraft and Participate in Development of Mouse Cerebellum," *Cell* 68: 33–51, 1992.

Suri et al., "Catecholaminergic Cell Lines from the Brain and Adrenal Glands of Tyrosine Hydroxylase–SV40 T Antigen Transgenic Mice," *The Journal of Neuroscience* 13(3): 1280–1291, 1993.

Timsit et al., "Oligodendrocytes Originate in a Restricted Zone of the Embryonic Ventral Neural Tube Defined by DM–20 mRNA Expression," *The Journal of Neuroscience* 15(2):1012–1024, 1995.

Warf et al., "Evidence for the Ventral Origin of Oligodendrocyte Precursors in the Rat Spinal Cord," *The Journal of Neuroscience* 11(8): 2477–2488, 1991.

Weiss et al., "Multipotent CNS Stem Cells Are Present in the Adult Mammalian Spinal Cord and Ventricular Neuroaxis," *The Journal of Neuroscience* 16(23): 7599–7609, 1996.

White and Whittemore, "Immortalization of Raphe Neurons: an Approach to Neuronal Function in vitro and in vivo," *Journal of Chemical Neuroanatomy* 5: 327–330, 1992.

Williams et al., "The Generation of Neurons and Oligodendrocytes from a Common Precursor Cell," *Neuron* 7: 685–693, 1991.

Yu et al., "Embryonic Expression of Myelin Genes: Evidence for a Focal Source of Oligodendrocyte Precursors in the Ventricular Zone of the Neurol Tube," *Neuron* 12: 1353–1362, 1994.

* cited by examiner

HUMAN SPINAL CORD CELL LINES AND METHODS OF USE THEREFOR

CROSS-REFERENCE TO RELATED APPLICATION

This application claims the benefit of Provisional Application No. 60/076,567, filed Mar. 2, 1998.

TECHNICAL FIELD

The present invention relates generally to human spinal cord cell lines. The invention is more particularly related to conditionally-immortalized spinal cord cell lines capable of differentiation into neurons, and to differentiated cells derived from such cell lines. Such cell lines and/or differentiated cells may be used in the development of therapeutic agents for the prevention and treatment of spinal cord-related diseases and injuries, as well as pain. The present invention is also related to the use of such cell lines and/or differentiated cells within various assays and for the study of spinal cord cell development and differentiation.

BACKGROUND OF THE INVENTION

The spinal cord plays a critical role in the functioning of the central nervous system (CNS). Although the spinal cord is the simplest region of the CNS, it contains diverse neural cell types which are interconnected in intricate patterns. During embryonic development, multi-potent stem cells in the neural tube proliferate and then ultimately differentiate into neurons and glia according to extrinsic cues and intrinsic determinants. Diseases and injuries that affect the functioning of spinal cord neural cells are often debilitating, and generally remain difficult to treat effectively.

To develop improved therapies for such disorders, further study of human spinal cord neurons and the differentiation process is needed. To date, such study has been hampered by the difficulty of obtaining sufficient primary human CNS tissue for research and the limited lifespan of primary cultures. In fact, research to date has failed to even demonstrate the existence of neuronal-restricted precursor cells in the human fetal spinal cord. As a result of the difficulties associated with performing human spinal cord research, the differentiation process remains poorly understood and the development of therapies for spinal cord diseases and injuries has been impeded.

Accordingly, there is a need in the art for stable spinal cord lines that can be readily differentiated, and can be used in the development of therapies for spinal cord-related conditions. The present invention fulfills these needs and further provides other related advantages.

SUMMARY OF THE INVENTION

Briefly stated, the present invention provides conditionally-immortalized human spinal cord cell lines capable of differentiation into neurons. In one aspect, the present invention provides methods for producing a conditionally-immortalized human spinal cord neural precursor cell, comprising the steps of: (a) transfecting human spinal cord cells plated on a first surface and in a first growth medium that permit proliferation with DNA encoding a selectable marker and an externally regulatable growth-promoting gene; and (b) selecting the transfected cells on a second surface and in a second growth medium that permit attachment and proliferation, and therefrom producing a conditionally-immortalized human spinal cord neural precursor cell. Within certain embodiments, the first and second surfaces are independently selected from the group consisting of substrates comprising one or more of a polyamino acid (e.g., polylysine or polyornithine), fibronectin, laminin or tissue culture plastic. Similarly, in certain embodiments, the growth-promoting gene may be an oncogene, such as v-myc, and expression of the growth-promoting gene may, but need not, be inhibited by tetracycline.

Within other aspects, the present invention provides conditionally-immortalized human spinal cord neural precursor cells capable of differentiation into neurons such as motoneurons.

The present invention further provides methods for producing neurons, comprising culturing a conditionally-immortalized human spinal cord neural precursor cell as described above under conditions inhibiting expression of the growth-promoting gene. Within certain embodiments, the cell may be cultured in medium comprising tetracycline and/or in the presence of one or more differentiating agents such as NGF, CNTF and BDNF. Within related aspects, the present invention provides neurons, such as motoneurons, produced as described above.

The present invention further provides methods for transplanting a human spinal cord cell into a mammal, comprising administering to a mammal a cell, including neurons, produced as described above. Within related aspects, methods are provided for treating a spinal cord-related condition in a patient, comprising administering to a patient a cell, including neurons, produced as described above.

In other aspects, methods are provided for screening for an agent that modulates an activity of a protein produced by a human spinal cord cell, comprising: (a) contacting a cell produced as described above with a candidate agent; and (b) subsequently measuring the ability of the candidate agent to modulate an activity of a protein produced by the cell.

Within further aspects, the present invention provides methods for detecting the presence or absence of a protein in a sample, comprising: (a) contacting a sample with a cell produced as described above; and (b) subsequently detecting a response in the cell, and therefrom detecting the presence of a protein in the sample.

The present invention also provides methods for identifying a human spinal cord gene or protein, comprising detecting the presence of a gene or protein within a culture of cells produced as described above.

In further aspects, methods are provided for screening for an agent that affects human spinal cord cell death, comprising: (a) contacting a cell produced as described above with a candidate agent under conditions that, in the absence of candidate agent, result in death of the cell; and (b) subsequently measuring the ability of the candidate agent to affect the death of the cell.

The present invention also provides methods for screening for a protein that regulates human spinal cord cell death, comprising: (a) altering the level of expression of a protein within a cell produced as described above; and (b) subsequently measuring the effect of the alteration on the death of the cell, and therefrom identifying a protein that regulates human spinal cord neural precursor cell death.

Within still other aspects, the present invention provides conditionally-immortalized human spinal cord neural precursor cells produced as described above. Such cells may be present within a clonal cell line.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS

FIGS. 1A and 1B are live phase contrast micrographs of immortalized human spinal cord cells. FIG. 1A shows the cells after growth in proliferative conditions. FIG. 1B shows the cells after 5 days of differentiation with DMEM/F12 medium containing N2 supplements, chick embryo extract (0.3%), laminin (5 μg/ml), tetracycline (1 μg/ml), CNTF (ciliary neurotrophic factor; 10 ng/ml) and NGF (nerve growth factor; 100 ng/ml).

In FIGS. 3A and 3C, the cells were plated in DMEM/F12 medium containing N2 supplements, fibronectin (5 μg/ml) and chick embryo extract (0.3%). FGF-2 or EGF was added at the concentrations indicated. In FIGS. 3B and 3D, the cells were plated in DMEM/F12 medium containing N2 supplements, FGF-2 (50 ng/ml), EGF (50 ng/ml) and chick embryo extract (0.3%) in 24-well plates pre-coated with fibronectin at the concentrations indicated. HSP1 was plated at a density of $2\times10^3$ cells/well and the cell number was counted on day 4. HSP2 was plated at a density of $2\times10^4$ cells/well and the cell number was counted on day 3. Data are shown as the mean±standard deviation of 4 replicates, with the Student's t-test for significance indicated for differences between cultures grown in the presence and absence of growth factor (a: $p<0.05$; b: $p<0.01$).

FIGS. 6A–6D are photographs showing the immunoreactivities for cell-type specific markers in representative clone HSP2 after 2 weeks of differentiation. FIGS. 6A and 6B show labeling for GFAP (glial fibrillary acidic protein; FIG. 6A) and A2B5 (6B) in the same field. FIG. 6C shows immunofluorescence for A2B5 in differentiated neurons in a different field. FIG. 6D shows double-labeling for GFAP (FITC) and neurofilament 200 kD (Texas Red).

DETAILED DESCRIPTION OF THE INVENTION

As noted above, the present invention is generally directed to conditionally-immortalized human spinal cord cell lines, differentiated cells generated from such cell lines and various methods employing such cells. In particular, the present invention is directed to conditionally-immortalized human spinal cord neural precursor cells that are capable of differentiation into neurons, and to the use of such cells for drug discovery and development, transplantation studies, therapeutic methods and a variety of assays. Conditionally-immortalized human spinal cord neural precursor cell lines of the present invention may, but need not, be clonal cell lines. The cell lines described herein provide an infinite, renewable supply of homogeneous cells and facilitate drug development for spinal cord disorders.

Conditionally-immortalized human spinal cord neural precursor cells may generally be prepared from human spinal cord tissue (e.g., fetal spinal cord tissue). Such tissue is preferably dissected from the spinal column, with the meninges and peripheral nerves removed. Spinal cord tissue is then dissociated, washed and plated on a surface and in a growth medium that permits proliferation (i.e., the surface and medium permit at least about 1% of the cells to double in a 24 hour period). One preferred growth medium contains DMEM/F-12 with N2 and B27 supplements (GIBCO, Baltimore, Md.), FGF-2 (human recombinant, 50 ng/ml, Boehringer Mannheim, Indianapolis, Ind.), EGF (human recombinant, 50 ng/ml, GIBCO, Baltimore, Md.), IGF-I (human recombinant insulin-like growth factor, 10 ng/ml, R & D Systems), PDGF (human recombinant platelet-derived growth factor, 10 ng/ml, Boehringer Mannheim, Indianapolis, Ind.), chick embryo extract (0.3%, GIBCO, Baltimore, Md., ultrafiltered), and bovine plasma fibronectin (5 μg/ml, Sigma, St. Louis, Mo.). Suitable surfaces include, but are not limited to, one or a combination of polyamino acids (e.g., polylysine and/or polyomithine), tissue culture plastic and surfaces treated with laminin or fibronectin. Cells may generally be plated at a density ranging from $10^3$ to $10^5$ cells/$cm^2$, preferably at a density of approximately $10^4$ cells/$cm^2$.

Human spinal cord neural precursor cells may be conditionally immortalized by transfection of the plated cells with any suitable vector containing a growth-promoting gene (i.e., a gene encoding a protein that, under appropriate conditions, promotes growth of the transfected cell) such that the production and/or activity of the growth-promoting protein is regulatable by an external factor. In a preferred embodiment the growth-promoting gene is an oncogene such as, but not limited to, v-myc. Other oncogenes that may be used as growth promoting genes include N-myc, c-myc, p53, SV40 large T antigen, polyoma large T antigen, E1a adenovirus and E7 protein of human papillomavirus. In general, a "growth promoting gene" is any gene that, when employed within a tet-controlled expression system as described herein, results in the generation of cultures of neural precursor cells which can be differentiated into neurons and motoneurons.

External regulation of the growth-promoting protein may be achieved by placing the growth-promoting gene under the control of an externally-regulatable promoter (i.e., a promoter whose activity may be controlled by, for example, modifying the temperature of the transfected cells or the composition of the medium in contact with the cells). In general, regulation of expression of the growth-promoting gene should be relatively tight (i.e., expression of the growth-promoting gene should generally be undetectable by immunofluorescent techniques as described herein when the promoter is repressed. For example, a tetracycline (tet)-controlled gene expression system may be employed (see Gossen et al., *Proc. Natl Acad. Sci. USA* 89:5547–5551, 1992; Hoshimaru et al., *Proc. Natl. Acad. Sci. USA* 93:1518–1523, 1996). In the absence of tet, a tet-controlled transactivator (tTA) within this vector strongly activates transcription from $ph_{CMV^*-1}$, a minimal promoter from human cytomegalovirus fused to tet operator sequences. tTA is a fusion protein of the repressor (tetR) of the transposon-10-derived tet resistance operon of *E. coli* and the acidic domain of VP16 of herpes simplex virus. Low, non-toxic concentrations of tet (0.01–1.0 µg/mL) almost completely abolish transactivation by tTA (ie., v-myc is no longer detectable using an immunofluorescence assay as provided herein).

In a preferred embodiment, the vector further contains a gene encoding a selectable marker (e.g., a protein that confers drug resistance). The bacterial neomycin resistance gene ($neo^R$) is one such marker that may be employed within the present invention. Cells carrying $neo^R$ may be selected by means known to those of ordinary skill in the art, such as the addition of 100–200 µg/mL G418 to the growth medium. It will be readily apparent that other markers may be employed, and appropriate selections may be readily performed by those of ordinary skill in the art.

Transfection may be achieved by any of a variety of means known to those of ordinary skill in the art including, but not limited to, retroviral infection. In general, plated cells may be transfected by infection with a suitable retrovirus (e.g., VSV-G pseudotyped LINX v-myc retrovirus, as described further below). The use of VSV-G pseudotyped retrovirus is preferred, in order to obtain higher stock concentrations of virus, to obtain stocks in the medium of choice (after centrifugation) and to increase the infectivity of human cells. Recently developed (nontraditional) VSV-G pseudotyped retroviral vectors may be especially useful for the infection of human cells, since the receptor for the VSV-glycoprotein is more abundant and less species-specific than the receptors for traditional amphotropic envelope proteins. Moreover, VSV-G pseudotyped viral particles have been reported to withstand ultracentrifugation, allowing concentration of virus and resuspension in growth medium compatible with neural progenitor cell growth (Burns et al., *Proc. Natl. Acad. Sci. USA* 90:8033–8037, 1993).

For example, a human spinal cord neural precursor cell culture prepared as described above may be infected within two days after plating by incubation for about 12–24 hours (e g., overnight) with retrovirus in the presence of polybrene (4–8 µg/mL). Retrovirus may then be removed by washing with fresh growth medium. Transfected cells carrying a selectable marker may generally be selected on a surface and in a growth medium that permit attachment and proliferation. Proliferation may be assessed as described above. The ability of a surface to permit attachment may be determined using visual microscopic inspection. In general, at least about 20% of the cells should adhere to the surface. One preferred growth medium contains DMEM/F-12 with N2 and B27 supplements (GIBCO, Baltimore, Md.), FGF-2 (human recombinant, 50 ng/ml, Boehringer Mannheim, Indianapolis, Ind.), EGF (human recombinant, 50 ng/ml, GIBCO, Baltimore, Md.), IGF-I (human recombinant insulin-like growth factor, 10 ng/ml, R & D Systems), PDGF (human recombinant platelet-derived growth factor, 10 ng/ml, Boehringer Mannheim, Indianapolis, Ind.), chick embryo extract (0.3%, GIBCO, Baltimore, Md., ultrafiltered), and bovine plasma fibronectin (5 µg/ml, Sigma, St. Louis, Mo.). Suitable surfaces include, but are not limited to, one or a combination of a polyamino acid (e.g., polylysine and/or polyomithine), tissue culture plastic and surfaces treated with laminin or fibronectin, as described above, and should grow as an adherent monolayer. The majority of the cells are generally polyconal, with very short processes.

Following transfection, cultures may be maintained in a simplified growth medium containing, for example, DMEM/F-12 with N2 supplement, FGF-2 (50 ng/ml), EGF (50 ng/ml), chick embryo extract (0.3%), and bovine plasma fibronectin (5 µg/ml). Cultures approaching confluence may be passaged by trypsinization and split 1:5. Typically, one T75 flask near confluence may yield $10^7$ cells, and cultures may be passaged every 3 to 4 days. Cells may also be frozen in liquid nitrogen for long-term storage.

Clonal cell lines may be isolated from a conditionally-immortalized human spinal cord neural precursor cell line prepared as described above. In general, such clonal cell lines may be isolated using standard techniques, such as by limit dilution or using cloning rings, and expanded. Clonal cell lines may generally be fed and passaged as described above. Genomic Southern blots may be performed to confirm clonality.

Conditionally-immortalized human spinal cord neural precursor cell lines (which may, but need not, be clonal) may generally be induced to differentiate into neurons (and, in some instances, glia) by inhibiting the expression of the growth-promoting gene (ie., suppressing the production and/or activity of the growth-promoting protein). For example, if the gene encoding the growth-promoting protein is under the control of an externally-regulatable promoter, the conditions (e.g., temperature or composition of medium) may be modified to suppress transcription of the growth-promoting gene. For the tetracycline-controlled gene expression system discussed above, differentiation may be achieved by the addition of tetracycline to suppress transcription of the growth-promoting gene. In general, 1–5 µg/mL tetracycline for 48 hours is sufficient to begin neuronal morphological differentiation, and the number of differentiated neurons increases during subsequent days. Such differentiation may be performed, for example, by plating the cells on a suitable substrate (e.g., laminin or tissue culture plastic) in a medium consisting of DMEM/F12 containing N2 supplements, chick embryo extract (0.3%), natural mouse laminin (5 µg/ml), FGF-2 (1–10 ng/ml) and tetracycline (1–5 µg/ml). In addition, agents that raise cyclic AMP, such as forskolin (10 µM) and/or neurotrophic factors may be included in the medium to enhance motoneuron differentiation (e.g., CNTF (10 ng/ml), NGF (100 ng/ml)

and BDNF (brain-derived neurotrophic factor; 10 ng/ml)). Culture medium may then be refreshed (e.g., every 5 days) using medium without FGF-2.

Characterization of both progenitor and differentiated cell lines may generally be performed using techniques well known to those of ordinary skill in the art, including morphological analysis of cell type, immunocytochemistry and PCR (to identify cell type-specific markers and receptors and to confirm the presence of the growth-promoting gene) and electrophysiological analysis of voltage- and ligand-gated currents. Briefly, neuronal cells may be identified morphologically based on the presence of phase bright cell bodies and long, thin processes. Neuronal markers include NCAM, βIII-tubulin and neurofilament (160 and 200 kD). Glial markers include GFAP (astrocyte) and the oligodendrocyte markers O1, O4 and GalC (galactose cerebroside). The presence or absence of such markers may be readily determined using standard immunofluorescence techniques (employing, for example, commercially available primary antibodies and fluorescent reagents) and the levels of mRNA encoding such markers may be determined using PCR or hybridization techniques. Electrophysiological analyses familiar to those of ordinary skill in the art may be employed to evaluate the ability of the cells to fire action potentials and to express sodium, calcium and potassium currents, as well as ligand-gated currents (e.g., N-methyl-D-aspartate (NMDA), kainate (KA) and γ-amino-n-butyric acid (GABA)), thereby determining the levels of functional channels and receptors.

Within certain aspects, the conditionally-immortalized human spinal cord neural precursor cell lines described herein may be introduced into a mammal for transplantation studies or for treatment of a patient. For example, cells may be introduced by grafting into the nervous system of animals such as rats, mice or monkeys. Studies may address the differentiation of the cells when transplanted into the developing or adult spinal cord or brain. The ability of the cells to serve as therapeutic agents in pathological conditions can also be examined. In particular, the cells themselves may have the capacity to finctionally replace neurons that die in neurodegenerative disorders or due to injury, or may serve as sources of agents (such as trophic factors) that have therapeutic benefit. Such agents may be produced by endogenous genes or by genes transfected into the cells.

For treatment of a patient, conditionally-immortalized human spinal cord neural precursor cell lines and/or modulating agents (which may inhibit or enhance an activity of a protein produced by a human spinal cord neural precursor cell, as described below) may be administered to a patient (either prophylactically or for treatment of an existing condition). Conditions that may be prevented and/or treated using such cells and/or modulating agents include, but are not limited to, motoneuron diseases (e.g., amyotrophic lateral sclerosis and spinal muscular atrophy), myelin-related diseases (e.g., multiple sclerosis), spinal cord injuries and pain. Cells may generally be introduced into the patient (i.e., transplanted) as described above. Modulating agents may be administered by any of a variety of routes known to those of ordinary skill in the art. Such agents may be administered in their active form, as prodrugs (i.e., compounds that are converted to the active form within the patient) or as nucleic acid sequences encoding the modulating agent or prodrug. Conditionally-immortalized human spinal cord neural precursor cells for use in this aspect of the present invention may, but need not, be further transfected such that they express one or more additional proteins (such as modulating agents) within the patient.

For administration to a patient, one or more conditionally-immortalized human spinal cord neural precursor cells (and/or modulating agents) are generally formulated as a pharmaceutical composition. A pharmaceutical composition may be a sterile aqueous or non-aqueous solution, suspension or emulsion, which additionally comprises a physiologically acceptable carrier (i.e., a non-toxic material that does not interfere with the activity of the active ingredient). Any suitable carrier known to those of ordinary skill in the art may be employed in the pharmaceutical compositions of the present invention. The selection of a carrier will depend, in part, on the nature of the substance (i.e., cells or chemical compounds) being administered. Representative carriers include physiological saline solutions, gelatin, water, alcohols, natural or synthetic oils, saccharide solutions, glycols, injectable organic esters such as ethyl oleate or a combination of such materials. Optionally, a pharmaceutical composition may additionally contain preservatives and/or other additives such as, for example, antimicrobial agents, anti-oxidants, chelating agents and/or inert gases, and/or other active ingredients.

Routes and frequency of administration, as well as doses, will vary from patient to patient and on the nature of the substance being administered. In general, the pharmaceutical compositions may be administered intravenously, intramuscularly, subcutaneously or intracavity. Doses are preferably administered daily. A suitable dose is an amount that is sufficient to show improvement in the symptoms of a patient afflicted with a spinal cord-related condition or to inhibit the onset of such a condition. Symptom improvement may be detected based on improvement and/or delay in clinical symptoms associated with the disease. In general, the amount of modulating agent present in a dose, or produced in situ by DNA present in a dose, ranges from about 1 mg to about 200 mg per kg of host. Suitable dose sizes will vary with the size of the patient, but will typically range from about 0.1 mL to about 5 mL for 10–60 kg animal.

Within certain aspects of the present invention, conditionally-immortalized human spinal cord neural precursor cell lines may be used in a variety of in vitro assays and screens. It will be apparent that the cell lines described herein may be used within numerous well known assays and screens, and that specific parameters and criteria for performing these methods will depend upon the assay being performed. Those of ordinary skill in the art can readily design specific assays and screens based upon well known methods and upon the desired properties of the compounds to be identified.

Within certain assays, the differentiated or undifferentiated conditionally-immortalized human spinal cord neural precursor cell lines described herein may be used to detect the presence or absence of a nucleic acid molecule or protein of interest in such cells. To detect a particular nucleic acid sequence (ie., DNA and/or RNA) within such cells, the well known methods of PCR and/or various hybridization techniques may be employed. Such assays may be readily designed and performed using methods described, for example, in Sambrook et al., *Molecular Cloning: A Laboratory Manual*, Cold Spring Harbor Laboratories, Cold Spring Harbor, N.Y., 1989. To detect a protein, the detection reagent is typically an antibody, which may be prepared as described below. There are a variety of assay formats known to those of ordinary skill in the art for using an antibody to detect a protein in a sample. See, e.g., Harlow and Lane, *Antibodies: A Laboratory Manual*, Cold Spring Harbor Laboratory, 1988. Antibodies for use in such assays may be polyclonal or monoclonal. Antibodies may be prepared by any of a variety of techniques known to those of ordinary skill in the art and monoclonal antibodies specific for a protein of interest may be prepared, for example, using the technique of Kohler and Milstein, *Eur. J. Immunol.* 6:511–519, 1976, and improvements thereto. Alternatively, a protein may be detected based upon its activity, using any suitable assay known in the art.

Such assays may generally be used, for example, within methods to evaluate the ability of an agent to modulate an activity of a protein produced by a human spinal cord neural precursor cell or a neuron. Within such assays, differentiated or undifferentiated cells may be contacted with a candidate agent under conditions and for a time sufficient to permit an agent to modulate protein activity. Following contact, the ability of the candidate agent to modulate an activity of a protein produced by the cell is measured using standard techniques, such as PCR or hybridization (for evaluating levels of MRNA) or any of a variety of immunoassays or functional assays appropriate for the protein of interest. For example, calcium-sensitive or voltage-sensitive dye coupled assays, cAMP measurements and/or receptor binding assays may be employed to evaluate the effect of a candidate modulating agent. In general, a suitable amount of antibody or other agent for use in such a screen will vary depending on the particular protein, but will range from about 10 $\mu$g to about 100 mg.

The term "modulation," as used herein, includes the suppression or enhancement of an activity of a protein of interest. Such modulation may occur at the transcriptional or translational level, or may be the result of altering the activity of the intact protein. Modulation of protein activity may be direct (i.e., the modulating agent may interact directly with the protein of interest) or may be indirect (i.e., the modulating agent may alter the expression and/or activity of one or more other proteins which in turn modulate the activity of the protein of interest). Modulating agents may be antibodies (e.g., monoclonal), polynucleotides or other drugs. Agents that modulate the activity of any cellular protein may be identified within such screens. In certain embodiments, modulating agents may be identified for proteins such as neurotransmitter receptors (e.g., AMPA-preferring receptors, kainate receptors, GABA receptors, adenosine receptors and/or 5-HT receptors), growth factor receptors (e.g., receptors for FGF-2, EGF, BDNF, NGF, CNTF, NT-3 and/or GDNF) or ion channels (e.g., sodium channels, calcium channels and/or potassium channels). Preferred modulating agents are able to suppress or enhance the activity of a protein by at least a factor of 2.

In another aspect of the present invention, the cell lines described herein may be used within a system for studying protein and/or gene expression in a native cellular environment. For example, receptor expression and/or activity may be assayed, and the effect of various modifications on such expression and/or activity may be evaluated using methods well known to those of ordinary skill in the art. In one such method, cell lines may be permanently or transiently transfected with one or more genes of interest such as, but not limited to, genes that produce or modify membrane proteins, secreted proteins or intracellular proteins of interest. Such genes include ion channels, neurotransmitter receptors, $\beta$-amyloid and/or MAP kinases. The transfected genes may also be coupled to reporter genes for use in drug development. Within this and other aspects described herein, conditionally-immortalized human spinal cord neural precursor cells may be employed without differentiation, or differentiated cells may be used. In addition, cells of varying ages and grown in any of a variety of conditions may be employed. The cell lines of the present invention have many advantages over existing cell lines for such studies, including the ability to provide clonal cell lines capable of producing neurons, and the property of conditional-immortalization, which allows arrest at specific stages of development. The selection of particular cells for any given study will depend on the goals of the study, and those of ordinary skill in the art will be readily able to prepare appropriate cells using the techniques described herein.

Within further aspects, conditionally-immortalized human spinal cord neural precursor cell lines of the present invention may be used in assays to detect the presence or absence of a particular protein in a sample. In general, an assay may be performed by contacting such cells with a sample and then measuring a response induced by the protein within the cells using methods familiar to those of ordinary skill in the art. For example, a response may be measured using differential display techniques.

In a further aspect, the conditionally-immortalized human spinal cord neural precursor cell lines described herein may be used in the identification of novel genes and proteins present in human spinal cord neural precursor cells. Techniques, such as PCR, differential display, hybridization, expression library screens, immunoassays and two-hybrid screens may be employed for such identification. A particularly useful technique is differential gene screening. Clonal cell lines as described herein are particularly suited to such studies because they are derived from a single parental cell and, therefore, human spinal cord neural precursor cell-specific genes are amplified with respect to non-clonal cell lines. Novael genes and proteins that are expressed upon experimental manipulation (e.g., induction of apoptosis) may also be identified.

The cell lines provided herein may also be used in in vitro models of neuronal cell death including, but not limited to, neuronal apoptosis induced by growth factor withdrawal. Briefly, a clonal conditionally-immortalized human spinal cord neural precursor cell line may be differentiated under conditions designed to minimize the basal level of apoptosis. Suitable conditions may be readily identified by evaluating the percentage of apoptotic nuclei in cells grown under different test conditions. The percentage of apoptotic nuclei may generally be determined by methods well known to those of ordinary skill in the art, such as by DAPI staining or the in situ nick end-labeling assay. Suitable conditions for minimizing basal apoptosis include differentiation in the presence of 1 $\mu$g/mL tetracycline, CNTF (10 ng/mL), NGF (100 ng/mL) and BDNF (10 ng/mL). Cells should be maintained in suitable differentiation conditions for a time sufficient to allow differentiation, while minimizing the basal level of apoptosis (which generally increases during the first 10 days of differentiation).

Such differentiated neuronal cells may then be employed in any of several models of apoptosis. In one such model, growth factors and N2 supplement are withdrawn for an amount of time sufficient to significantly increase the percentage of apoptotic cells with condensed nuclei. Preferably, the percentage of such apoptotic cells increases by at least about two fold. Under the representative conditions described above, about 18 hours of withdrawal is generally sufficient. A significant percentage of the cells should be rendered nonviable. Preferably, at least about 50% of the neurons are no longer viable following withdrawal of growth factors.

Regardless of the particular model, the cells may be used to study the mechanisms of apoptosis, as well as the effect of various conditions and agents on the apoptosis of neuronal cells, using experimental techniques well known to those of ordinary skill in the art. For example, the cells may be used to screen for an agent that affects neuronal cell death. Such a screen may be performed by contacting the cells during growth factor withdrawal with a candidate agent and then evaluating the ability of the candidate agent to affect the subsequent level of apoptosis. Similarly, the cells may be used to screen for a protein that regulates neuronal cell death. In such a screen, the level of expression or activity of a candidate protein (e.g., an enzyme) is altered within the cells (using standard techniques) and then the affect of the alteration on the level of apoptosis following treatments (including, but not limited to, growth factor withdrawal) is measured.

The following Examples are offered by way of illustration and not by way of limitation.

EXAMPLES

Example 1

Preparation of Human Spinal Cord Progenitor Cell Lines

This Example illustrates the conditional immortalization of human spinal cord progenitor cells.

Human spinal cord cells in primary culture were prepared from human fetal spinal columns, of 8 to 9 weeks gestational age (obtained through Advanced Bioscience Resources, Inc.). The tissue was procured in compliance with state and federal laws and regulations. Prior to dissection, spinal columns were maintained for approximately 24 hours at 4° C. in Hank's balanced salt solution (with no calcium or magnesium) containing penicillin (50 I.U./ml) and streptomycin (50 $\mu$g/ml). The spinal cord was dissected from the spinal column, and meninges and peripheral nerves were removed. The spinal cord tissue was then dissociated by incubation at 37° C. for 30 to 45 minutes in an enzyme solution containing 0.2% collagenase plus dispase, with occasional trituration. The dispersed spinal cord cells were washed 3 times in high-glucose Dulbecco's modified Eagle medium (DMEM)/F-12 (1:1). The cells were subsequently plated at a density of approximately $10^4$ cells/cm$^2$ in growth medium consisting of DMEM/F-12 with N2 and B27 supplements (GIBCO, Baltimore, Md.), FGF-2 (human recombinant, 50 ng/ml, Boehringer Mannheim, Indianapolis, Ind.), EGF (human recombinant, 50 ng/ml, GIBCO, Baltimore, Md.), IGF-I (human recombinant, 10 ng/ml, R & D Systems), PDGF (human recombinant, 10 ng/ml, Boehringer Mannheim, Indianapolis, Ind.), chick embryo extract (0.3%, GIBCO, Baltimore, Md., ultrafiltered), and bovine plasma fibronectin (5 $\mu$g/ml, Sigma, St. Louis, Mo.).

For retroviral infection, the LINX v-myc vector was employed (Hoshimaru et al., *Proc. Natl. Acad Sci. USA* 93:1518–1523, 1996; Sah et al., *Nature Biotechnol.* 15:574–580, 1997). In this system, in the absence of tetracycline, a tetracycline-controlled transactivator (tTA) strongly activates transcription from Ph$_{CMV^*-1}$, resulting in the expression of the downstream v-myc oncogene. Tetracycline (0.01–1.0 $\mu$g/ml) almost completely abolishes transcriptional activation by tTA, thereby blocking transcription of the v-myc oncogene. A gene conferring neomycin resistance is also present in the vector. Spinal cord cultures were retrovirally infected and G418- selected using methods analogous to those described by Sah et al., *Nature Biotechnol.* 15:574–580, 1997.

After G418 selection, cultures were maintained in a simplified growth medium consisting of DMEM/F-12 with N2 supplement, FGF-2 (50 ng/ml), EGF (50 ng/ml), chick embryo extract (0.3%) and bovine plasma fibronectin (5 $\mu$g/ml). Cultures approaching confluence were passaged by trypsinization and split 1:5. Typically, one T75 flask near confluence yielded $10^7$ cells, and cultures were passaged every 3 to 4 days.

Figure 1A:
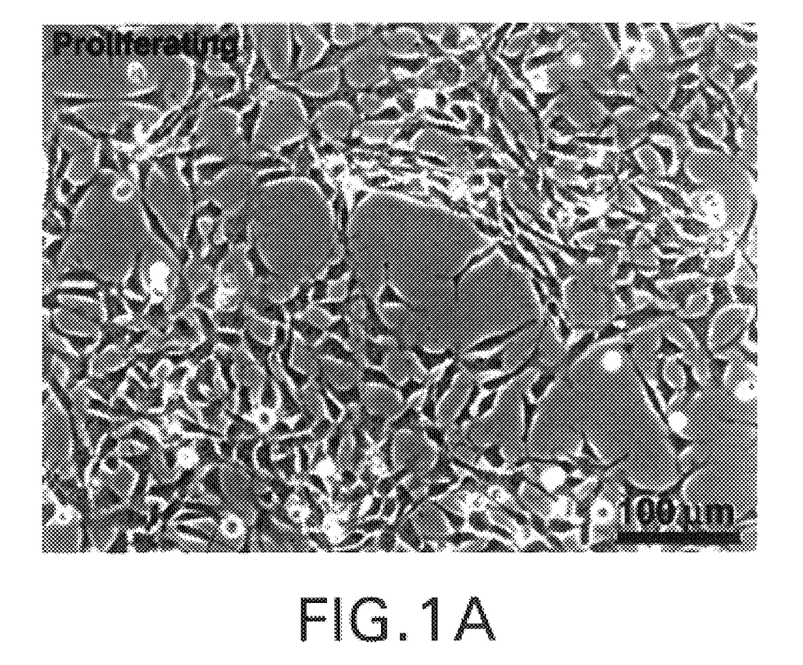

During G418 selection, some cell death occurred; after the selection, v-myc$^+$cells became the predominant cell type in the culture. These G418-resistant, v-myc$^+$cells grew as an adherent monolayer. The majority of the cells were polygonal with very short processes (FIG. 1A).

To isolate clonal cell lines, half a cell, on average, was seeded into each well of a 96-well plate. Out of 2000 wells, 279 wells contained single colonies, which were expanded by feeding and passaging them as described above.

Most of these single colonies grew as adherent monolayers; only 4 colonies formed aggregates loosely attached to the substrate. These four colonies were designated HSP1, HSP2, HSP3 and HSP4, and expanded further. All four putative clones grew as adherent monolayers when the cells were passaged frequently; however, with less frequent passaging, cell aggregates formed. Cells with fine neuronal processes were occasionally seen in HSP1. Three of the putative clones (HSP1, HSP2 and HSP4) grew well and were subsequently characterized.

For immunocytochemistry, cultures were fixed with methanol, and were incubated with primary antibody in blocking buffer (PBS, 1% normal donkey serum, 0.1% Triton X-100) for 2 hours at room temperature, rinsed with PBS, and then incubated with a fluorescein (FITC)- or Texas red-conjugated species-specific secondary antibody (Jackson Immunoresearch Laboratories, Inc., West Grove, Pa.) in blocking buffer for another hour at room temperature. Cultures were then rinsed three times with PBS and coverslipped with PVA/DABCO before scoring and photographing representative fields.

Figure 2:
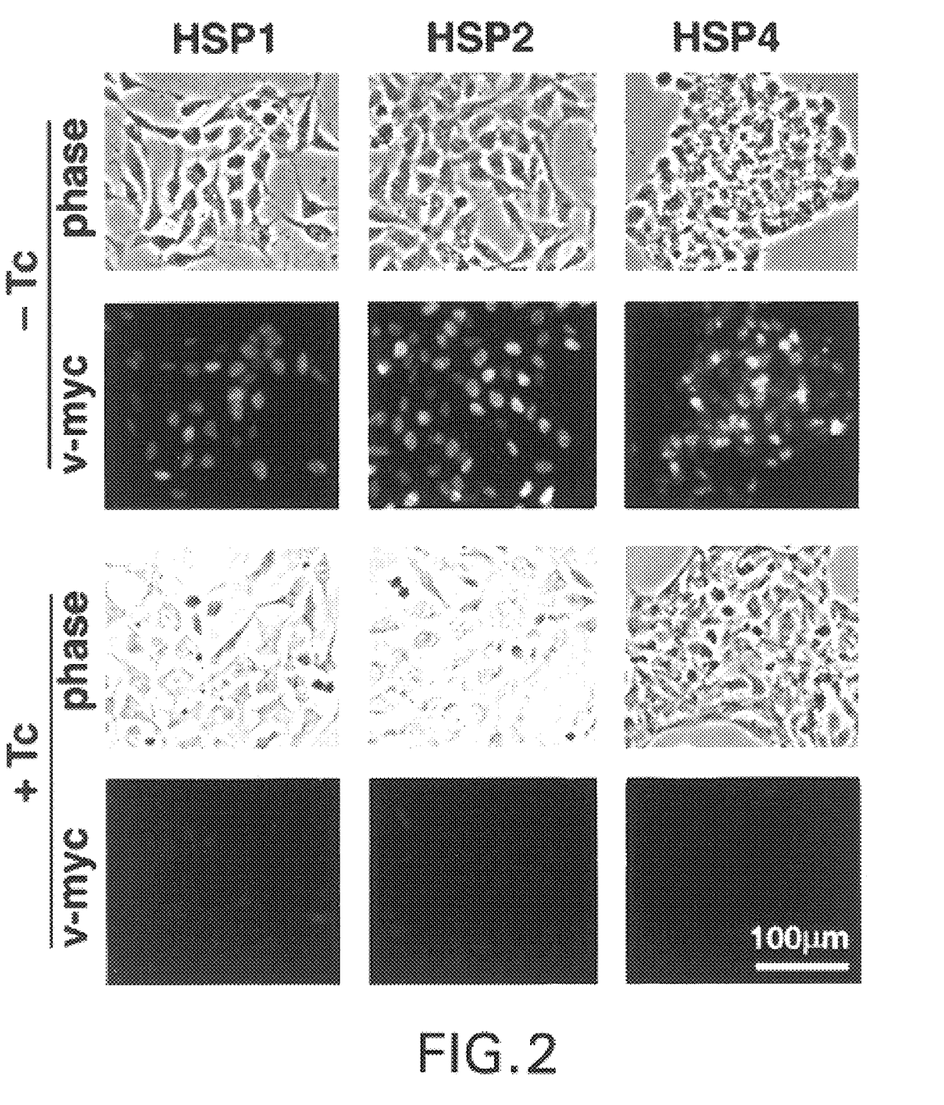
FIG. 2 is a set of live phase contrast micrographs (phase) and photographs showing labeling for v-myc (v-myc) in representative immortalized human spinal cord clonal cell lines HSP1, HSP2 and HSP4, as indicated. The clones HSP1, HSP2 and HSP4 were cultured for 3 days in the proliferative growth condition with (+Tc) or without (−Tc) daily tetracycline (1 μg/ml) administration, as indicated, before being processed for v-myc immunofluorescence. For each field, a phase photograph (post-fixation) is shown immediately above the corresponding immunofluorescence photograph.

The v-myc oncoprotein was detected by immunofluorescence in the nuclei of HSP1, HSP2 and HSP4 cells when the cells were cultured in the absence of tetracycline (FIG. 2, −Tc). As expected, after addition of tetracycline, v-myc immunoreactivity was no longer detectable (FIG. 2, +Tc). These results indicate that the clonal cell lines described herein express v-myc in a tetracycline-regulatable manner.

Example 2

Differentiation of Conditionally-Immortalized Human Spinal Cord Progenitor Cells into Post-mitotic Neurons This Example illustrates the differentiation of the retrovirally infected progenitor cells into neurons.

Figure 1B:
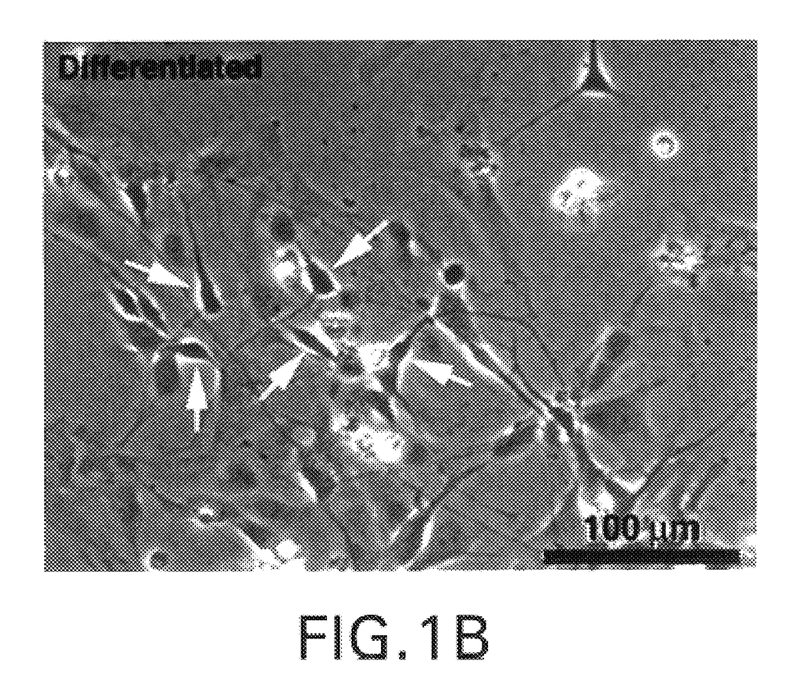

Bulk-infected cultures were plated at a density of 2×10$^4$ cells/cm$^2$ into differentiation medium (DMEM/F12 medium containing N2 supplements, FGF-2 (1–10 ng/ml), chick embryo extract (0.3%), natural mouse laminin (5 $\mu$g/ml), tetracycline (1–5 $\mu$g/ml) and a combination of neurotrophic factors [CNTF (10 ng/ml) and NGF (100 ng/ml)] known to enhance motoneuron differentiation). The culture medium was subsequently refreshed every 5 days with differentiation medium lacking FGF-2. Within 48 hours, a few cells with neuronal morphology were apparent. The number of differentiated neurons increased during the subsequent days. These neurons exhibited round somata with long processes (FIG. 1B). Most of these differentiated cells did not die upon fluorodeoxyuridine (80 μM) treatment for 10 days, indicating that they were post-mitotic. Cultures were generally differentiated for 7–14 days prior to immunocytochemical staining and for 4–20 days prior to electrophysiological recording.

Example 3

Growth Requirements of Human Spinal Cord Cell Lines

This Example illustrates the effect of growth factors on cell lines as provided herein.

Figure 3A:
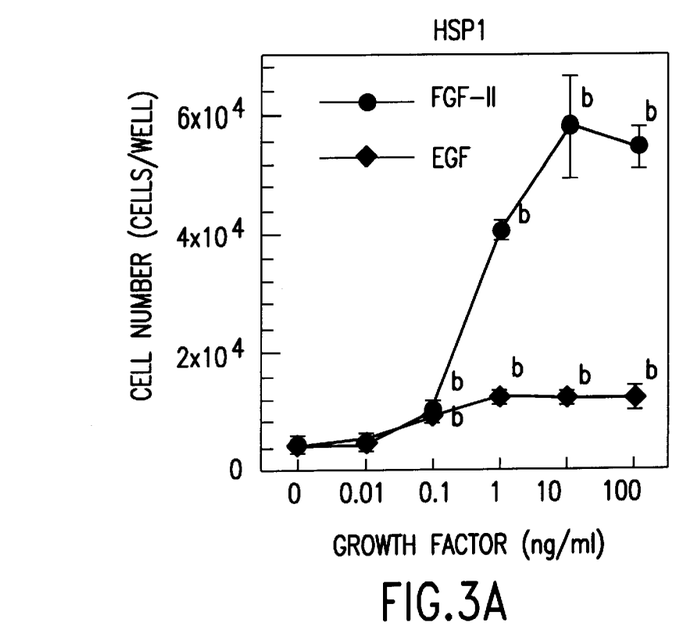
FIGS. 3A–3D are graphs showing the effects of FGF-2 (basic fibroblast growth factor), EGF (epidermal growth factor) and fibronectin on the proliferation of the representative clones HSP1 (FIGS. 3A and 3B) and HSP2 (FIGS. 3C and 3D).
Figure 3B:
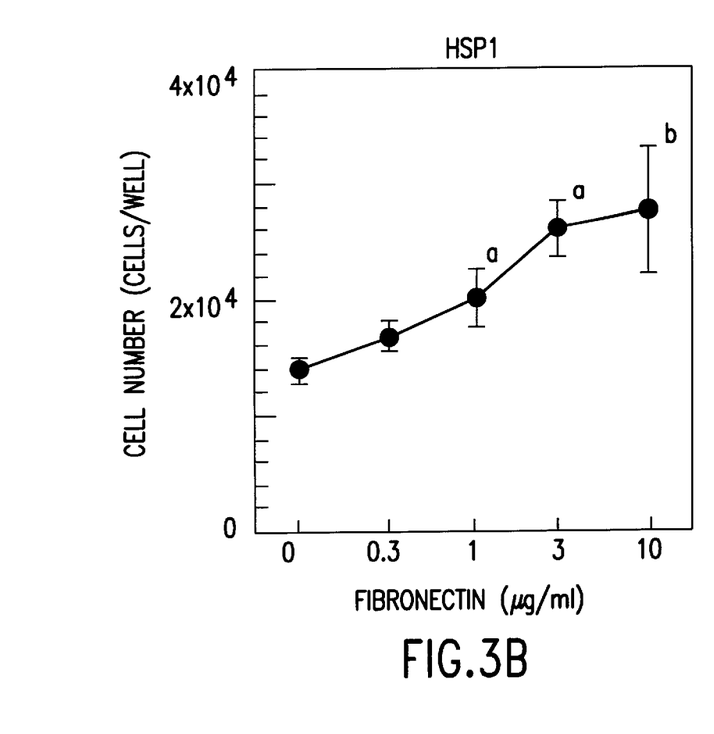
Figure 3C:
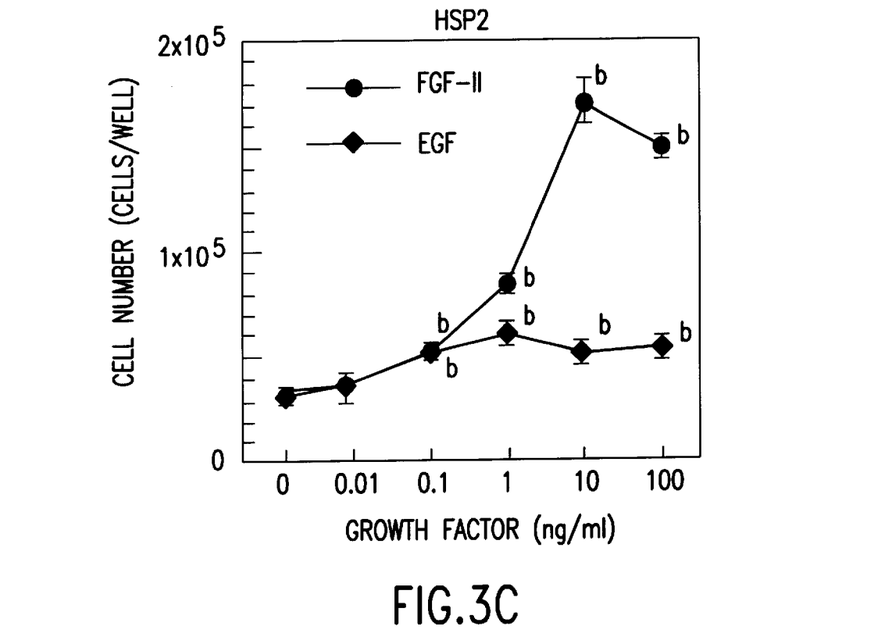
Figure 3D:
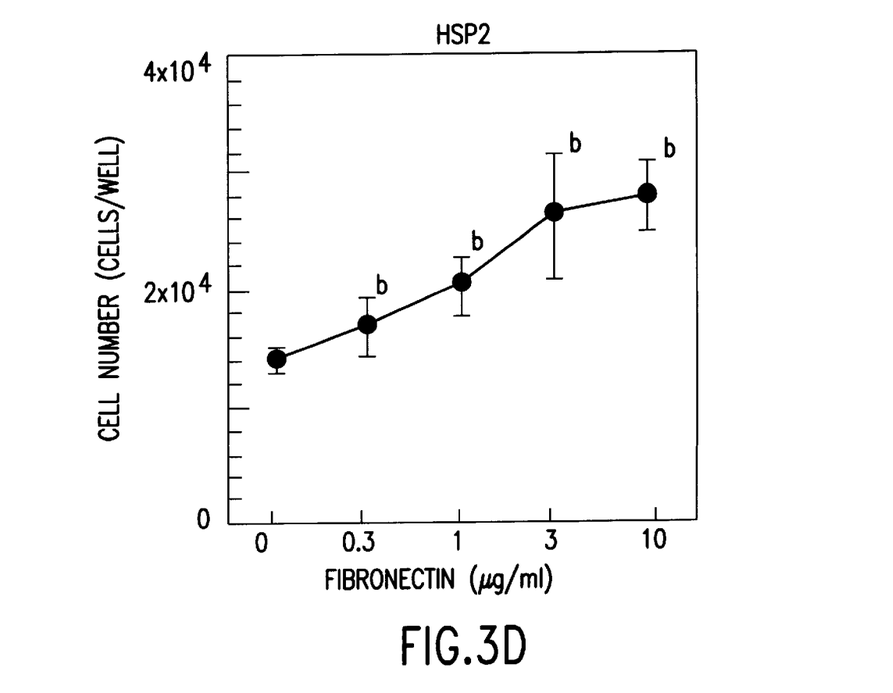

The proliferation of HSP1, HSP2 and HSP4 cell lines required growth factors;

FGF-2 stimulated proliferation strongly whereas EGF increased proliferation to only a small extent (FIG. 3A). Unlike neuronal restricted precursors from the rat spinal cord (Mayer-Proschel et al., *Neuron* 19:773–785, 1997), the growth rates of HSP1, HSP2 and HSP4 were unaffected by the presence of NT-3 (10 ng/ml). The threshold for the growth promoting activity of FGF-2 was 0.1 ng/ml whereas maximal growth promoting activity occurred at 10 ng/ml (FIGS. 3A and 3C). Stimulation of proliferation by EGF was maximal at 1 ng/ml (FIGS. 3A and 3C). Although the human spinal cord cell lines could attach, survive and proliferate without additional attachment factors, fibronectin enhanced cell proliferation (FIGS. 3B and 3D) by promoting cell attachment. The growth promoting effect of fibronectin saturated at 3 μg/ml.

Example 4

Characterization of Human Spinal Cord Cell Lines

This Example illustrates characterization of HSP1, HSP2 and HSP4 cell lines, as well as differentiated cells generated by these cell lines.

Neuronal markers were detected using immunocytochemical assays. The cultures were incubated with primary antibodies at 37° C. for 1 hour before methanol fixation. Primary antibodies used for immunocytochemistry included polyclonal antibodies against neurofilament 200 kD (1:800, Chemicon, Temecula, Calif.) and neurofilament 68 kD (1:400, Chemicon, Temecula, Calif), and monoclonal antibodies against MAP2a/b (1:100, Chemicon, Temecula, Calif.), neurofilament 68 kD (1:40, Sigma, St. Louis, Mo.), neurofilament 160 kD (1:400, Sigma, St. Louis, Mo.), neurofilament 200 kD (1:40, Sigma), NCAM (1:1, a gift from Dr. Manhendra Rao, also available from Developmental Studies Hybridoma Bank) and βIII tubulin (1:400, Sigma, St. Louis, Mo.). All primary antibodies were validated on positive and negative control cultures. Cultures were incubated with primary antibody in blocking buffer (PBS, 1% normal donkey serum, 0.1% Triton X-100) for 2 hours at room temperature, rinsed with PBS, and then incubated with a fluorescein (FITC)- or Texas red-conjugated species-specific secondary antibody (Jackson Immunoresearch Laboratories, Inc., West Grove, Pa.) in blocking buffer for another hour at room temperature. Cultures were then rinsed three times with PBS and coverslipped with PVA/DABCO before scoring and photographing representative fields.

Figure 4:
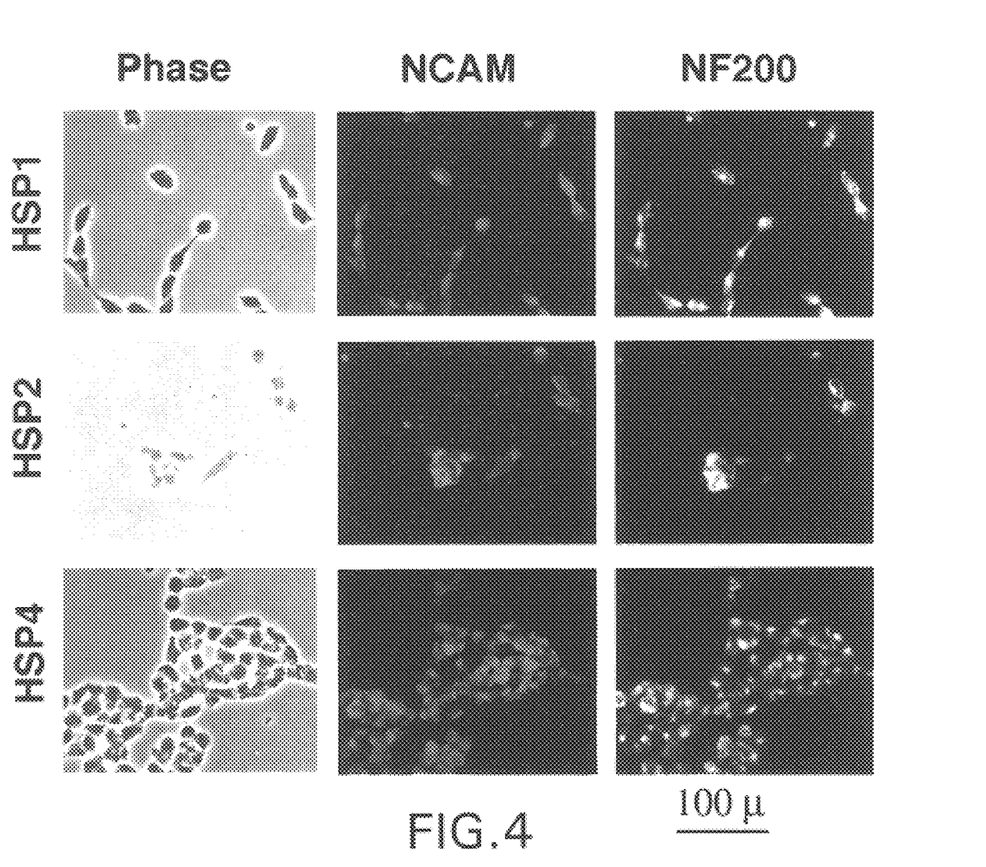
FIG. 4 is a series of photographs showing immunofluorescence labeling for NCAM (neural cell adhesion molecule) and NF200 (neurofilament 200 kD) in the representative immortalized human spinal cord clonal cell lines HSP1, HSP2 and HSP4, as indicated. For each cell line, a phase photograph (post-fixation) is shown to the left of the corresponding immunofluorescence photographs, as indicated.
Figure 7A:
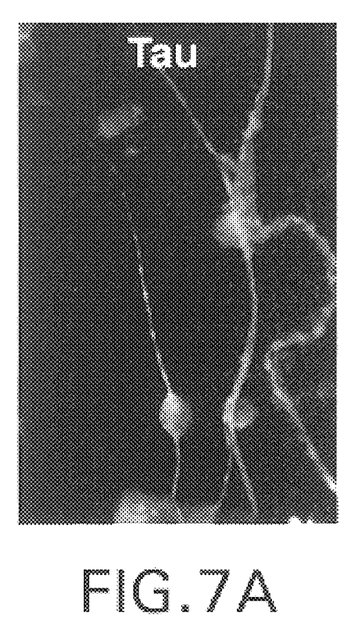
FIGS. 7A–7D are photographs illustrating the immunoreactivities for tau, MAP2a&b (microtubule associated protein), peripherin and synaptophysin, as indicated, in representative clone HSP1 after 17 days of differentiation.
Figure 7B:
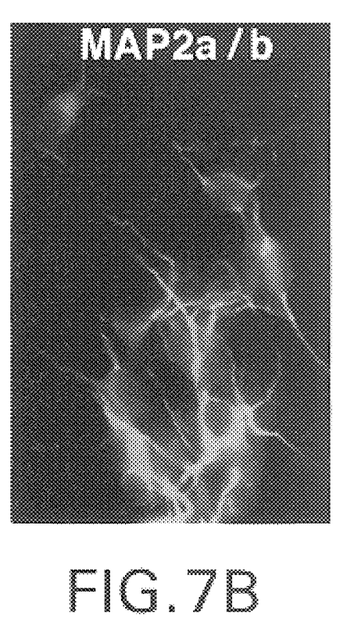
Figure 7C:
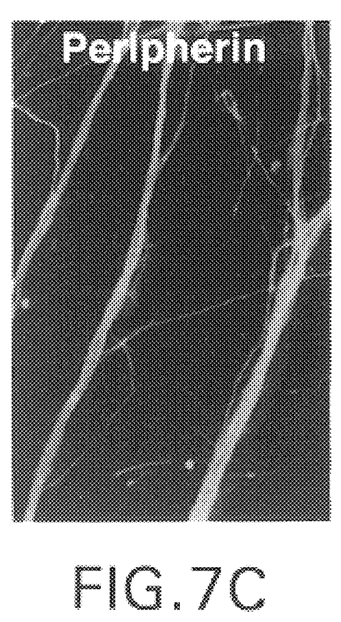
Figure 7D:
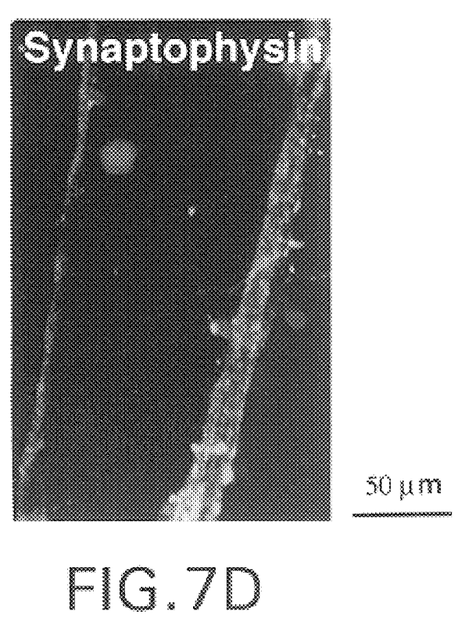

In the proliferative condition, over 90% of HSP1, HSP2 and HSP4 cells expressed neuronal markers such as neurofilament (both 200 and 68 kD), βIII-tubulin and NCAM (FIG. 4) whereas MAP2a/b-immunoreactivity was absent. Neurofilament (160 kD)-immunoreactivity was present to a lesser extent, in approximately 30% of HSP1, HSP2 and HSP4 cells. After differentiation with DMEM/F12 medium containing N2 supplements, CNTF, NGF, BDNF, chick embryo extract, laminin and tetracycline (3 μg/ml), neurofilament (200, 160 and 68 kD)- and MAP2a/b-(FIG. 7B) immunoreactivities were present in the cytoplasm and processes. The cellular distribution of all neurofilaments shifted from the cytoplasm to the processes after differentiation. Moreover, after differentiation, HSP1 cells expressed mature neuronal markers such as tau, peripherin and synaptophysin (FIGS. 7A, 7C and 7D).

These results indicate that neuronal-restricted precursor cell lines described herein express the neuronal markers neurofilament (160 and 200 kD), βIII-tubulin and NCAM in the proliferative growth condition. The presence of neurofilament (200 kD) has been described previously in proliferating spinal cord neuroblasts (Ray and Gage, *J. Neurosci.* 14:3548–3564, 1994). However, in contrast to the observations reported herein, proliferating neuronal-restricted neural precursors from the rat spinal cord that are NCAM-immunoreactive do not express βIII-tubulin or neurofilament (160 kD) (Mayer-Proschel et al., *Neuron* 19:773–785, 1997). Taken together, these findings suggest that human and rat neuronal-restricted precursor cells differ with respect to at least 2 cytoskeletal components.

Figure 5:
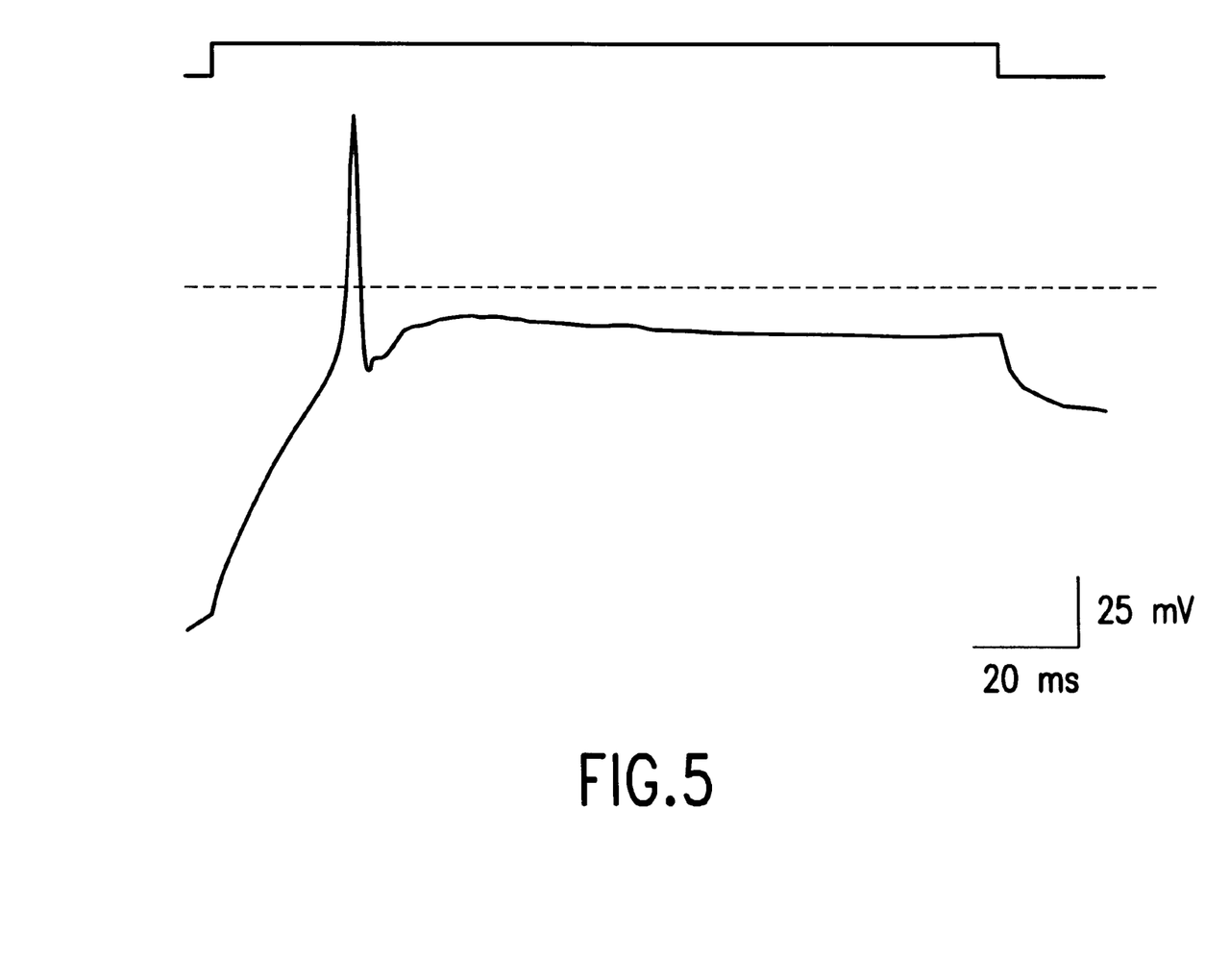
FIG. 5 depicts an electrophysiological recording of an action potential in an HSP1 cell after differentiation for 4 days. The top trace shows the injected current pulse whereas the lower trace shows the membrane potential of the cell. The dashed line indicates zero membrane potential.

After differentiation, not only did cells with neuronal morphology exhibit staining for all neuronal markers examined, but they also fired action potentials upon current injection (13 of 14 cells). The whole-cell configuration of the patch-clamp method was used to record action potentials in current clamp mode. The bath solution was Tyrode's (in mM, 150 NaCl, 4 KCl, 2 $MgCl_2$, 10 Glucose, 10 HEPES, pH adjusted to 7.4 with NaOH; 2 mM $CaCl_2$ and 4 mM $BaCl_2$ were added). Pipettes (2–4 MΩ resistance) were pulled from Boralex glass (Rochester Scientific, Rochester, N.Y.), and filled with internal solution containing (in mM) 130 KCl, 5 $MgCl_2$, 10 HEPES, 10 EGTA, pH adjusted to 7.4 with KOH. Action potentials were recorded using an Axopatch 200A patch clamp amplifier and the BASIC-FASTLAB interface system (INDEC Systems, Capitola, Calif.). FIG. 5 shows an example of an action potential in an HSP1 cell after 4 days of differentiation; in current clamp mode, a 150 msec, 104 pA current pulse elicited an action potential that reached a peak of +61 mV.

Figure 6A:
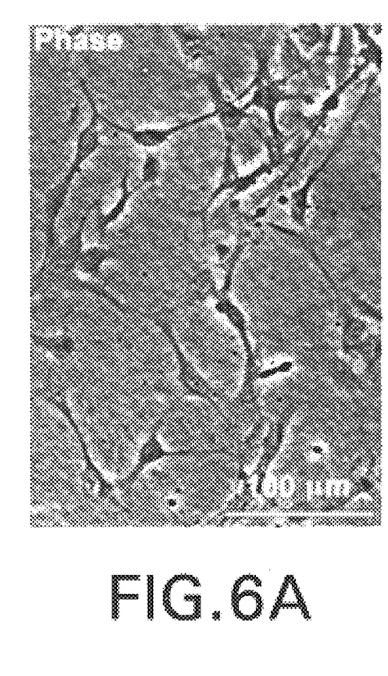
Figure 6B:
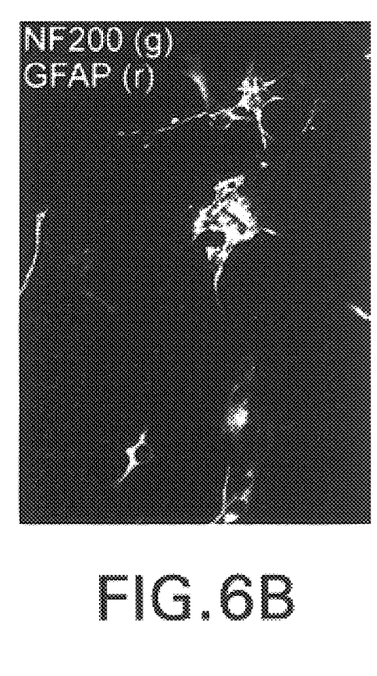
Figure 6C:
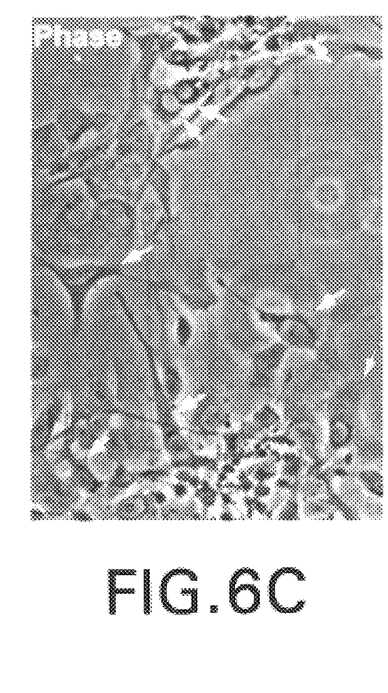
Figure 6D:
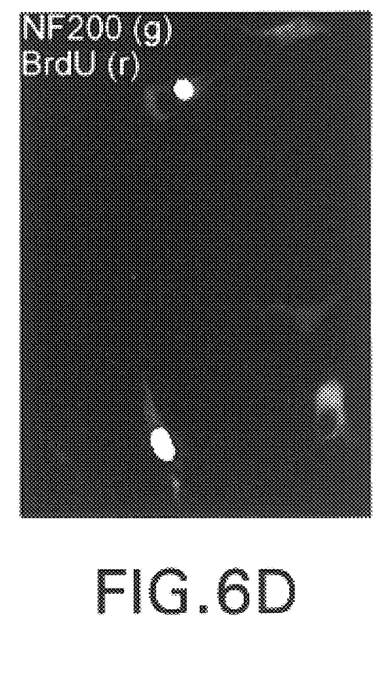

To determine if HSP1, HSP2 or HSP4 could give rise to glial cells, the cultures were stained for astrocyte (GFAP) and oligodendrocyte (O1, O4 and GalC) markers after differentiation with DMEM/F12 medium containing N2 supplements, CNTF, NGF, BDNF, chick embryo extract, laminin and tetracycline (3 μg/ml). Immunocytochemistry was performed as described above, except that primary antibodies were polyclonal antibodies against glutamate (1:15,000, Sigma, St. Louis, Mo.) and monoclonal antibodies against O4 (a gift from Dr. Manhendra Rao, also available from Chemicon, Temecula, Calif.), O1 (1:5, Boehringer Mannheim, Indianapolis, Ind.) and GalC (a gift from Dr. Manhendra Rao, also available from Chemicon, Temecula, Calif., and Sigma, St. Louis, Mo.). Only HSP2 gave rise to cells exhibiting GFAP immunoreactivity (<0.1% of cells, FIG. 6A) which did not co-localize with A2B5- or neurofilament 200 kD-immunoreactivities (FIGS. 6B–D). Oligodendrocyte markers (O1, O4 and GalC) were not detectable with immunocytochemistry in any of the cell lines under these conditions. Even the addition to the differentiation medium of CNTF and NT-3, which strongly promote oligodendrocyte differentiation in CNS stem cells (Lachyankar et al., *Exp. Neurol.* 144:350–360, 1997), did not result in the expression of oligodendrocyte markers.

HSP1 and HSP4 were differentiated in the presence of 5% fetal bovine serum to determine if the cell lines could be induced to differentiate into astrocytes under these conditions. After 3 days of differentiation with tetracycline plus 5% fetal bovine serum, virtually no cells remained viable, indicating that this human spinal cord cell line responds to serum in a manner similar to that of neuronal-restricted precursors from the rat spinal cord.

The human spinal cord cell lines differentiated into multiple types of spinal cord neurons, including motoneurons, and expressed different excitatory and inhibitory neurotransmitters. To examine the neuron subsets obtained from the cell lines described herein, cultures were examined by immunofluorescence for glutamate, GABA, choline acetyltransferase (ChAT), NGFR and Islet-1. The cultures were fixed with 1% glutaraldehyde in a 3% sucrose solution for glutamate and GABA detection by immuno-alkaline phosphatase methods (Li et al., *Endocrine* 5:205–217, 1996). ChAT was detected by the APAAP method; briefly, after incubation with anti-ChAT antibody at 4° C. overnight, the cultures were incubated with anti-mouse IgG (Jackson Immunoresearch Laboratories, Inc., West Grove, Pa., 1:2000) for 1 hour, followed by incubation with APAAP (Sigma, St. Louis, Mo., 1:40) for 1 hour at 37° C. NTB/BCIP (Boehringer Mannheim, Indianapolis, Ind.) or Fast Red (Sigma, St. Louis, Mo.) was used as the substrate for alkaline phosphatase. Primary antibodies used for immunocytochemistry included polyclonal antibodies against glutamate (1:15,000, Sigma, St. Louis, Mo.) and GABA (1:1000, Chemicon, Temecula, Calif.) and monoclonal antibodies against choline acetyltransferase (1:5, Boehringer Mannheim, Indianapolis, Ind.).

Figure 8A:
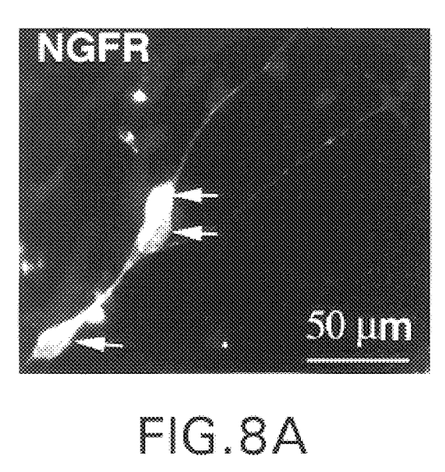
FIGS. 8A–8D are photographs illustrating the immunoreactivities for NGFR (low affinity nerve growth factor receptor), peripherin, NGFR/Islet-1 (homeodomain transcription factor) and ChAT (choline acetyltransferase), as indicated, in representative clone HSP1 after 3, 3, 15 or 17 days respectively.
Figure 8B:
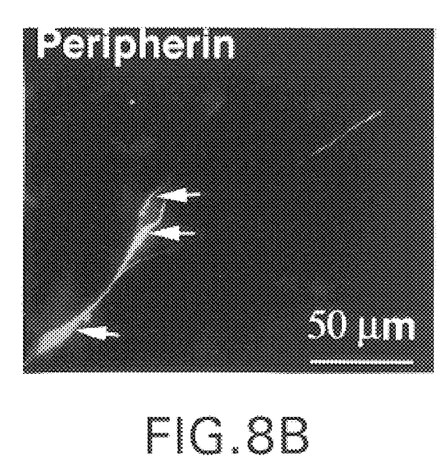
Figure 8C:
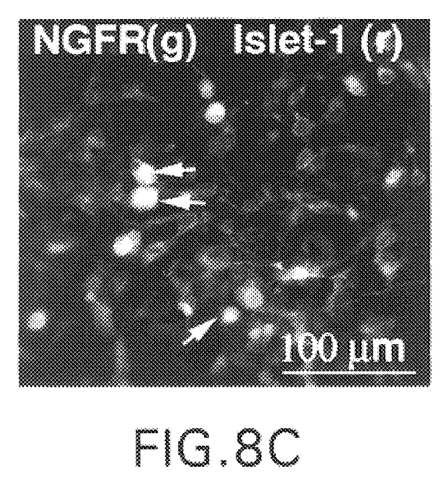
Figure 8D:
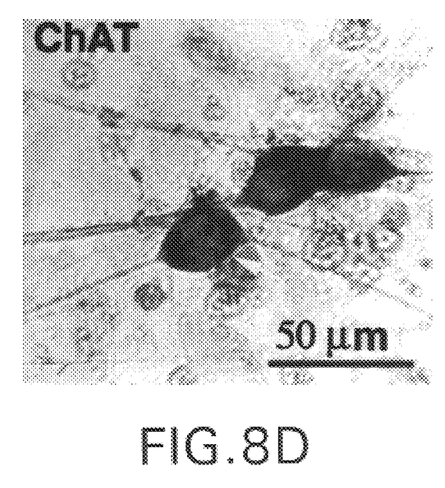
Figure 9:
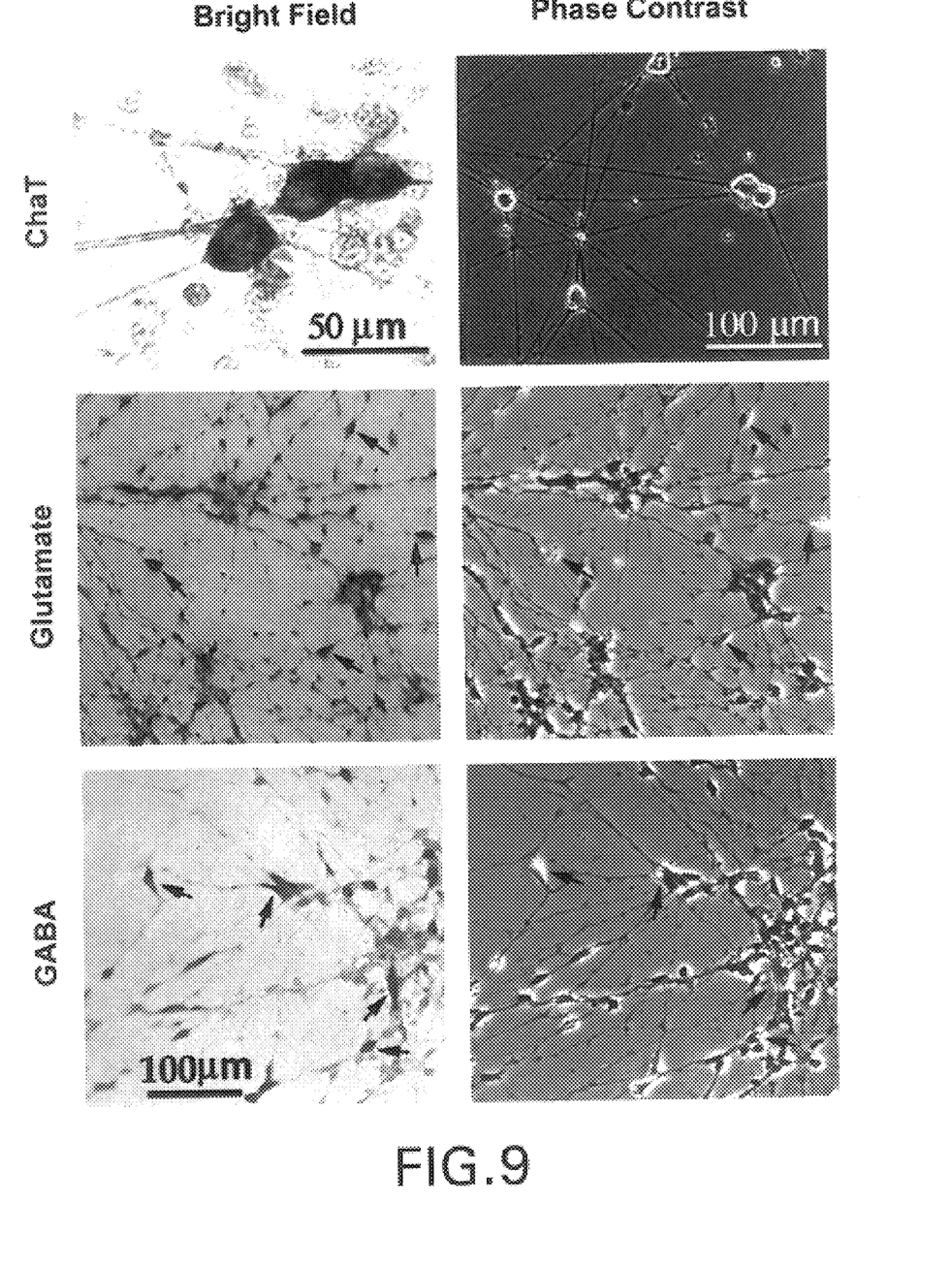
FIG. 9 is a set of photographs illustrating the immunoreactivities for ChAT, glutamate and GABA (γ-aminobutyric acid), as indicated, in representative clone HSP1 after 7 days of differentiation. For each field, a phase photograph (post-fixation) is shown immediately to the right of the corresponding immunostaining photograph. Examples of positively- and negatively-stained cells are indicated by arrows and arrowheads, respectively.

Immunoreactivity for ChAT, the synthetic enzyme for acetylcholine (which is specific to the motoneuron lineage), was detected in 23±9% of differentiated HSP1 neurons (FIGS. 8D and 9), consistent with motoneuron phenotype. The presence of immunoreactivity for NGFR and Islet-1 (FIG. 8) further confirmed the motoneuron phenotype. After HSP1 differentiation, glutamate-immunoreactivity was detected in every neuron whereas GABA-immunoreactivity, consistent with interneuron phenotype, was present in 45±6% of the neurons (FIG. 7). These results indicate that neuronal restricted precursor cell lines from the human spinal cord are useful for examining extrinsic and intrinsic signals that direct the differentiation of specific subsets of spinal cord neurons. Moreover, these results establish that these immortalized human spinal cord cell lines can be differentiated into motoneurons.

From the foregoing, it will be appreciated that, although specific embodiments of the invention have been described herein for the purpose of illustration, various odifications may be made without deviating from the spirit and scope of the invention.

What is claimed is:

1. A method for producing a conditionally-immortalized human spinal cord neural precursor cell, comprising:

(a) transfecting human spinal cord cells plated on a first surface and in a first growth medium that permit proliferation with DNA encoding a selectable marker and an externally regulatable growth-promoting gene; and (b) selecting the transfected cells on a second surface and in a second growth medium that permit attachment and proliferation, and therefrom producing a conditionally-immortalized human spinal cord neural precursor cell.

2. The method of claim 1 wherein the first and second surfaces are independently selected from substrates comprising one or more of a polyamino acid, fibronectin, laminin or tissue culture plastic.

3. The method of claim 1 wherein the growth-promoting gene is an oncogene.

4. The method of claim 3 wherein the oncogene is v-myc.

5. The method of claim 1 wherein expression of the growth-promoting gene is inhibited by tetracycline.

6. A conditionally-inmortalized human spinal cord neural precursor cell that differentiates into neurons following suppression of production or activity of a protein encoded by an externally regulated growth-promoting gene.

7. The conditionally-immortalized human spinal cord neural precursor cell according to claim 6, wherein the cell differentiates into motoneurons following suppression of production or activity of a protein encoded by an externally regulated growth-promoting gene.

8. A method for producing neurons, comprising culturing the cell produced according to claim 1 under conditions inhibiting expression of the growth-promoting gene.

9. The method according to claim 8, wherein the cell is cultured in medium comprising tetracycline.

10. The method according to claim 8, wherein the cells are cultured in the presence of one or more differentiating agents.

11. The method according to claim 10, wherein the differentiating agent is selected from the group consisting of nerve growth factor, ciliary neurotrophic factor, and brain-derived neurotrophic factor.

12. A neuron produced according to the method of claim 8.

13. A motoneuron produced according to the method of claim 8.

14. A conditionally-immortalized human spinal cord neural precursor cell produced according to the method of claim 1.

15. A cell according to claim 14, wherein the cell is present within a clonal cell line.

* * * * *